United States Patent [19]

Bauer et al.

[11] 4,210,654
[45] Jul. 1, 1980

[54] ANTISEBORRHEIC PREPARATIONS

[75] Inventors: Robert Bauer, Bettingen; Hans U. Hostettler, Arlesheim, both of Switzerland

[73] Assignee: Hoffmann-La Roche Inc., Nutley, N.J.

[21] Appl. No.: 941,444

[22] Filed: Sep. 11, 1978

[30] Foreign Application Priority Data

Sep. 14, 1977 [CH] Switzerland ............ 11213/77

[51] Int. Cl.$^2$ ............................................ A61K 31/44
[52] U.S. Cl. ................................ 424/263; 252/547; 424/DIG. 4
[58] Field of Search .................. 424/263, DIG. 4; 252/547

[56] References Cited

U.S. PATENT DOCUMENTS 4,007,261  2/1977  Sorrentino et al. .............. 424/70

FOREIGN PATENT DOCUMENTS 1337467 11/1973 United Kingdom .

OTHER PUBLICATIONS

Handbuch der Kosmetik und Reichstoffe, vol. III, p. 618.
Dictionnaire Vidal, 1968, pp. 1177 & 1196.
Aromox Aminoxide Technical Bulletin L-37/1 "Aromox Amine Oxides" Armour Chemicals Ltd. Harrogate, England.
J. Soc. Cosmet. Chem. 26, pp. 155-168.

*Primary Examiner*—Allen J. Robinson
*Attorney, Agent, or Firm*—Jon S. Saxe; George M. Gould; R. Hain Swope

[57] ABSTRACT

Antiseborrheic preparations for application to the skin, hair and scalp containing pyridoxine tripalmitate are disclosed. The preparations of the invention contain as a solubilizer for the pyridoxine tripalmitate one or a mixture of amine oxides of the formula

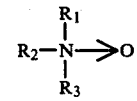

wherein $R_1$ is an alkyl group having 16 to 20 carbon atoms and each of $R_2$ and $R_3$ is hydroxy ethyl or methyl.

8 Claims, No Drawings

ANTISEBORRHEIC PREPARATIONS

BACKGROUND OF THE INVENTION

The present invention relates to cosmetic preparations containing pyridoxine tripalmitate. Pyridoxine tripalmitate is recognized in the art as possessing antiseborrheic properties. Creams containing pyridoxine tripalmitate have been described, for example, in Soaps-Oils-Fats-Waxes 26, p. 819 (1959). It was reported therein that, in tests with such creams, after a minimum of two weeks application to test subjects, general emollient and improvement effects on the skin and a slight sebaceous gland inhibiting action were noted.

It has been found in accordance with the present invention that pyridoxine tripalmitate will cause sebaceous gland inhibition within a comparatively short period of time when administered in a cosmetic preparation which is free of fats and oils and this rapidity of onset of antiseborrheic action of the preparations of the present invention is considered unexpected in view of the above-noted report in the literature.

DETAILED DESCRIPTION OF THE INVENTION

The present invention is concerned with cosmetic preparations possessing antiseborrheic activity. More particularly, the present invention is concerned with antiseborrheic preparations containing as the active ingredient pyridoxine tripalmitate.

In accordance with the present invention cosmetic preparations containing pyridoxine tripalmitate are provided which are effective antiseborrheic agents. The preparations of the invention are distinguished over similar preparations known to the art in that they contain no oils or fats. Heretofore, it was not recognized that preparations containing pyridoxine tripalmitate could be formulated without oils and fats.

In accordance with the present invention, pyridoxine tripalmitate is formulated into cosmetic preparations for application to the skin, hair and scalp with the aid of one or more amine oxides represented by the general formula

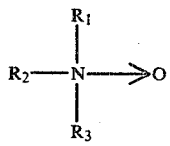

wherein $R_1$ is an alkyl group having 16 to 20 carbon atoms, and each of $R_2$ and $R_3$ is hydroxy ethyl or methyl.

Preferred amine oxides of formula I include octadecyldimethylamine oxide, dimethylhexadecylamine oxide, bis(hydroxyethyl)tallowamine oxide, hydrogenated dimethyltallowamine oxide and a mixture of dimethylhexadecylamine oxide and dimethyltetradecylamine oxide. The amine oxides of formula I are non-ionic surfactants available commercially, for example, under the tradename series Ammonyx from Millmaster-Onyx International and Aromox from the Armour Hess Division of AKZO Chemie. While it is preferred to use the amine oxides of formula I individually, it is within the purview of the present invention to use mixtures of two or more of them in any proportion.

In accordance with the present invention, preparations containing pyridoxine tripalmitate and the amine oxides of formula I are provided for application to the skin, hair and scalp. Such preparations contain from about 0.2% by weight to about 5% by weight, preferably from about 1% by weight to about 2% by weight pyridoxine tripalmitate and from about 0.1% by weight to about 10% by weight, preferably from about 0.1% by weight to about 2% by weight of one or a mixture of amine oxides for formula I.

In addition to the pyridoxine tripalmitate and the amine oxide, the cosmetic preparations of the invention contain carrier materials conventional in the art for such preparations, i.e. facial lotions, with our without alcohol, shampoos, hair treatments, creams and the like. Such carrier materials include, for example, stearic acid, cetyl alcohol, stearyl alcohol, a complex of alkylphosphate and diethanolamine marketed under the tradename Amphisol by Givaudan S. A., Vernier, a mixture of fatty acid sulfates marketed under the tradename Texapon CS by Henbel and Cie GmbH, allantoin-N-acetyl-methionate, menthol, $Al_2(OH)_5Cl$, sodium chloride, lactic acid, citric acid, tartaric acid, methyl p-hydroxybenzoate, propyl-p-hydroxybenzoate,2,2',4,4'-tetrahydroxybenzophenone, suitable perfumes and colors and the like. Facial lotions prepared in accordance with the invention can contain from 0% to about 50% by weight, preferably from about 0% to about 20% by weight alcohol.

Facial lotions prepared in accordance with the present invention were tested for sebaceous gland inhibiting action by the glass block method of Schaefer and Kuhn-Bussius, Arch. Klin. Exper. Derm. 238, p. 429–435 (1970). In this test it was demonstrated that the facial lotions prepared in accordance with the invention reduced the amount of measurable sebaceous matter by about 50% at two hours after application.

The following Examples serve to illustrate the instant invention, but are not to be construed as limiting said invention.

EXAMPLE 1

An antiseborrheic facial lotion was prepared from the following formulation

| Ingredient | Amount in Grams |
| --- | --- |
| Pyridoxine tripalmitate | 2.00 |
| Amonyx SO[1] | 8.00 |
| Lactic acid | 0.14 |
| Almeth[2] | 1.00 |
| Alcohol 95% | 47.38 |
| Menthol | 0.10 |
| Water | 41.38 |

[1] Octadecyldimethylamine oxide 25% - Millmaster-Onyx International.
[2] Allantoin-N-acetyl-DL-methionate - Nobel Hoechst Chimie.

Forty grams of water were warmed to 75°, combined with the Ammonyx SO and homogeneously mixed. The pyridoxine tripalmitate was melted at 80° and added to the mixture with rapid stirring. The lactic acid was mixed with 1.38 grams of water and introduced at 50°. The Almeth was then added. The menthol was then dissolved in the alcohol and added to the mixture at 40°. Thereafter, the mixture was stirred until it cooled to ambient temperature.

EXAMPLE 2

An antiseborrheic facial lotion was prepared from the following formulation

| Ingredient | Amount in Grams |
| --- | --- |
| Pyfidoxine tripalmitate | 2.00 |
| Ammonyx CO[1] | 6.67 |
| Lactic acid | 1.00 |
| Chlorhydrol | 2.25 |
| Perfume | 0.20 |
| Colorant | 0.10 |
| Alcohol 95% | 20.00 |
| Water | 67.78 |

[1]dimethylhexadecylamine oxide 30% - Millmaster-Onyx International.
[2]AL$_2$(OH)$_5$Cl - Reheis Chemical Company Sixty grams of water were warmed to 75°, combined with the Ammonyx CO and homogeneously mixed. The pyridoxine tripalmitate was melted at 80° and added to the mixture with rapid stirring. The lactic acid was mixed with 7.78 grams of water and introduced at 50°. The Chlorhydrol was then added. The perfume and colorant were dissolved in the alcohol and added to the mixture at 40°. Thereafter, the mixture was stirred until it cooled to ambient temperature.

EXAMPLE 3

Example 2 was repeated utilizing in place of Ammonyx CO a corresponding amount of Ammonyx MCO (a mixture of dimethylhexadecylamino oxide and dimethyltetradecylamino oxide 30%—Millmaster-Onyx International).

EXAMPLE 4

An antiseborrheic facial lotion was prepared from the following formulation

| Ingredient | Amount in Grams |
| --- | --- |
| Pyridoxine tripalmitate | 2.00 |
| Aromox T/12[1] | 4.08 |
| Citric acid | 0.32 |
| Alcohol 95% | 20.00 |
| Water | 73.60 |

[1]Bis(hydroxyethyl)tallowamine oxide 49% - AKZO Chemie/Armour Hess Division.

Example 5

Example 4 was repeated utilizing in place of Aromox T/12 a corresponding amount of Aromox DM 16 D(dimethylhexadecylamine oxide 39%—AKZO Chemie/Armour Hess Division).

EXAMPLE 6

Example 4 was repeated utilizing in place of Armox T/12 a corresponding amount of Aromox DMHTD(hydrogenated dimethyltallowamine oxide 39%—AKZO Chemie/Armour Hess Division).

EXAMPLE 7

An antiseborrheic facial lotion was prepared from the following formulation

| Ingredient | Amount in Grams |
| --- | --- |
| Pyridoxine tripalmitate | 2.00 |
| Aromox DM 18 D-W[1] | 8.00 |
| Lactic acid | 0.20 |
| Sodium chloride | 0.80 |
| Alcohol 95% | 20.00 |
| Colorant | 0.10 |
| Water | 68.90 |

[1]Dimethyloctadecylamine oxide 25% - AKZO Chemie/Armour Hess Division.

A total of 58.90 grams of water were warmed to 75° with the Aromox and homogeneously mixed. The pyridoxine tripalmitate was melted at 80° and added with rapid stirring. The lactic acid was mixed with 2 g. of water and introduced at 50°. The colorant was dissolved in the alcohol and added at 40°. The sodium chloride was dissolved in 8 g. of water and added. Thereafter, the mixture was stirred until it cooled to ambient temperature.

EXAMPLE 8

An antiseborrheic facial without alcohol was prepared from the following formulation

| Ingredient | Amount in Grams |
| --- | --- |
| Pyridoxine tripalmitate | 2.00 |
| Ammonyx SO | 8.00 |
| Lactic acid | 0.12 |
| Nipagin M[1] | 0.10 |
| Perfume | 0.10 |
| Water | 89.68 |

[1]Methyl p-hydroxybenzoate - NIPA Laboratories Ltd.

A total of 88 grams of water were warmed to 75° with the Ammonyx and Nipagin and homogeneously mixed. The pyridoxine tripalmitate was melted at 80° and added with rapid stirring. The lactic acid was mixed with 1.68 g. of water and introduced at 50°. The perfume was then added at 45°. Thereafter, the mixture was then stirred until it cooled to ambient temperature.

EXAMPLE 9

An antiseborrheic shampoo was prepared from the following formulation

| Ingredient | Amount in Grams |
| --- | --- |
| Pyridoxine tripalmitate | 2.00 |
| Texapon CS paste[1] | 33.00 |
| Ammonyx SO | 4.00 |
| Ammonyx MCO | 4.00 |
| Cetyl alcohol | 0.50 |
| Stearyl alcohol | 0.50 |
| Polyethyleneglycol-400-monostearate | 1.00 |
| Citric acid 10% | 4.40 |
| Colorant 0.2% | 4.00 |
| Preserving agent | 0.20 |
| Perfume | 0.40 |
| Water | 46.00 |

[1]Mixture of fatty alcohol sulfates - Henkel & Cie GmbH.

The Texapon CS paste, Ammonyx SO and MCO, water, cetyl alcohol, stearyl alcohol, polyethyleneglycol-400-monostearate and preserving agent were warmed together to 75° and homogeneously mixed. The pyridoxine tripalmitate was then melted at 80° and added with vigorous stirring. The citric acid solution was added at 50° and the colorant and perfume added at 45°. Thereafter, the mixture was stirred until it cooled to ambient temperature.

EXAMPLE 10

A hair treatment preparation useful against greasy hair was prepared from the following formulation

| Ingredient | Amount in Grams |
| --- | --- |
| Ammonyx SO | 8.000 |
| Uvinul D 50[1] | 0.025 |
| Pyridoxine tripalmitate | 2.000 |
| Tartaric acid powdered | 0.250 |
| Polyquart H 50%[2] | 1.500 |
| Water | 79.675 |
| BTC 2125 50%[3] | 0.200 |
| Perfume | 0.200 |
| Colorant | 0.150 |
| Sodium chloride solution 10% g/g | 8.000 |

[1] 2,2',4,4'-tetrahydroxy-benzophenone
[2] Polyglycol/polyamine condensation resin
[3] N-alkyl-dimethyl-benzyl-ammonium chloride, n-alkyl-dimethyl-ethyl-benzyl-ammonium chloride 69.675 grams of water and the Ammonyx were warmed to 75° C. and homogeneously mixed. The pyridoxine tripalmitate was melted at 80° and added with rapid stirring. The Uvinul D 50, tartaric acid, Polyquart H, 10 g. of water and BTC 2125 were warmed together to 50° and added to the formulation. The perfume, colorant and sodium chloride solution were successively added at 45°. Thereafter, the mixture was stirred until it cooled to ambient temperature.

EXAMPLE 11

An antiseborrheic cream was prepared from the following formulation.

| Ingredient | Amount in Grams |
| --- | --- |
| Water | 84.99 |
| Ammonyx SO | 8.00 |
| Nipagin M | 0.20 |
| Stearic acid | 2.50 |
| Pyridoxine tripalmitate | 2.00 |
| Cetyl alcohol | 0.50 |
| Stearyl alcohol | 0.50 |
| Amphisol[1] | 1.00 |
| Nipasol M[2] | 0.10 |
| Lactic acid | 0.16 |
| Perfume | 0.05 |
| ph value = 6.20 | |

[1] Complex compound of alkylphosphate and diethanolamine - Givaudan S.S., Vernier
[2] Propyl-p-hydroxybenzoate - NIPA Laboratories Ltd.

A total of 83.59 g. of water, the ammonyx SO and the Nipagin M were warmed together to 75° and homogeneously mixed. The stearic acid, pyridoxine tripalmitate, cetyl alcohol, stearyl alcohol, Amphisol and Nipasol M were melted at 80° and added to the aqueous mixture with vigorous stirring. Thereafter, the lactic acid was mixed with 1.40 g. of water and added at 50° to the formulation. The perfume was added at 45° and the mixture stirred until it cooled to ambient temperature. 9n

We claim:

1. An antiseborrheic composition comprising:
   (a) a cosmetically acceptable carrier suitable for application to the skin, hair and scalp, said carrier being substantially free from oils and fats, and
   (b) from about 0.2% by weight to about 5% by weight of pyridoxine tripalmitate and, as a solubilizer therefor, from about 0.1% by weight to about 10% by weight of one or more amine oxides of the formula

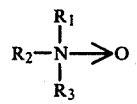

wherein $R_1$ is an alkyl group containing from 16 to 20 carbon atoms and each of $R_2$ and $R_3$ is methyl or hydroxyethyl.

2. A composition in accordance with claim 1 wherein pyridoxine tripalmitate is present in from about 1% by weight to about 2% by weight.

3. A composition in accordance with claim 1 wherein said amine oxides are present in from about 0.1% by weight to about 2% by weight.

4. A composition in accordance with claim 1 wherein said amine oxide is octadecyldimethylamine oxide.

5. A composition in accordance with claim 1 wherein said amine oxide is hexadecyldimethylamine oxide.

6. A composition in accordance with claim 1 wherein said amine oxide is bis(hydroxyethyl)tallowamine oxide.

7. A composition in accordance with claim 1 wherein said amine oxide is hydrogenated dimethyltallowamine oxide.

8. A composition in accordance with claim 1 wherein said amine oxide is a mixture of dimethylhexadecylamine oxide and dimethyltetradecylamine oxide.

* * * * *